(12) United States Patent
Kong et al.

(10) Patent No.: US 9,273,246 B2
(45) Date of Patent: Mar. 1, 2016

(54) TRIPHENYLENE DERIVATIVE AND USE THEREOF

(71) Applicant: JIANGSU HECHENG DISPLAY TECHNOLOGY CO., LTD., Jiangsu (CN)

(72) Inventors: Xianfei Kong, Jiangsu (CN); Ming Yan, Jiangsu (CN); Yudong Tan, Jiangsu (CN); Zhaoyuan Chen, Jiangsu (CN); Shizhi You, Jiangsu (CN)

(73) Assignee: Jiangsu Hecheng Display Technology Co., Ltd., Jiangsu (CN)

( * ) Notice: Subject to any disclaimer, the term of this patent is extended or adjusted under 35 U.S.C. 154(b) by 0 days.

(21) Appl. No.: 14/410,144

(22) PCT Filed: May 31, 2013

(86) PCT No.: PCT/CN2013/000642
§ 371 (c)(1),
(2) Date: Dec. 22, 2014

(87) PCT Pub. No.: WO2013/189171
PCT Pub. Date: Dec. 27, 2013

(65) Prior Publication Data
US 2015/0275087 A1 Oct. 1, 2015

(30) Foreign Application Priority Data
Jun. 21, 2012 (CN) .......................... 2012 1 0210009

(51) Int. Cl.
C07C 69/92 (2006.01)
C09K 19/32 (2006.01)
G02B 5/30 (2006.01)

(52) U.S. Cl.
CPC ............... *C09K 19/322* (2013.01); *C07C 69/92* (2013.01); *G02B 5/3016* (2013.01); *C09K 2019/328* (2013.01)

(58) Field of Classification Search
None
See application file for complete search history.

(56) References Cited

U.S. PATENT DOCUMENTS 5,518,783 A    5/1996  Kawata et al.
7,443,474 B2  10/2008  Ito et al.
7,495,730 B2   2/2009  Hisakado et al.

FOREIGN PATENT DOCUMENTS

CN   1128985 A      8/1996
CN   102757349 A   10/2012
GB   2279072 A     12/1994
JP   2003113141 A   4/2003

*Primary Examiner* — Yevegeny Valenrod
(74) *Attorney, Agent, or Firm* — Laurence A. Greenberg; Werner H. Stemer; Ralph E. Locher

(57) ABSTRACT

A triphenylene derivative of general formula (I) or general formula (II) which can be used as a component of liquid crystal medium and the use thereof are provided in the present invention. This compound can be used to form a negative discotic liquid crystal composition having a suitable temperature range of liquid crystal phase and a lower clearing point, which can be used in TFT liquid crystal display as an optical compensation film (cell) material.

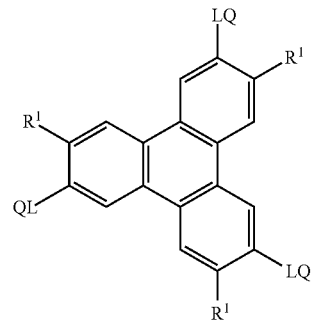

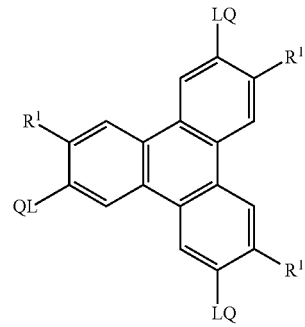

6 Claims, 1 Drawing Sheet

TRIPHENYLENE DERIVATIVE AND USE THEREOF

TECHNICAL FIELD

The present invention relates to a compound used as a component of liquid crystal medium, and the use thereof.

BACKGROUND ARTS

Rod-like liquid crystal materials having positive birefringence ($\Delta n>0$, $\Delta n=n_e-n_o$) are used in TFT liquid crystal display at present. Anisotropy of the rod-like liquid crystal materials will cause light leak of the display and result in a narrower viewing angle. In order to improve the viewing angle of the display, it is an effective method to compensate the optical path difference of line polarized light after passing through a liquid crystal cell by using an optical compensation film having negative birefringence ($\Delta n<0$). The optical compensation film materials reported currently comprise polymer films uniaxially or biaxially stretched, main chain liquid crystal macromolecules, macromolecules having rigid chain unit, photopolymerisable rod-like liquid crystal macromolecules and discotic liquid crystal compounds.

The birefringence of the triphenylene discotic liquid crystal having optically uniaxial nematic phase is negative, and its absolute value is close to that of the rod-like liquid crystal usually used in liquid crystal display. Therefore, the triphenylene discotic liquid crystal having optically uniaxial nematic phase can be used as an optical compensation film (cell) material to compensate the optical path difference of line polarized light after passing through a liquid crystal cell.

The use of hexaarylate of triphenylene compound having a nematic phase as optical compensation film material was reported in U.S. Pat. No. 7,495,730, U.S. Pat. No. 7,443,474 and U.S. Pat. No. 5,518,783. Such type of materials already reported mostly have a higher melting point (of above 100) and a clearing point of about 200. When used for preparing an optical compensation film, the material has to be heated to a temperature above the clearing point thereof, and then cooled slowly to control the orientation of the discotic molecules. Therefore, while ensuring that the liquid crystal phase temperature is in a suitable range, reducing the clearing point of the material can save energy and simplify preparation process. The melting point of a material must be lower than room temperature when used as an optical compensation cell material.

Therefore, there is a need for providing a liquid crystal material having a suitable temperature range of liquid crystal phase and a lower clearing point.

SUMMARY OF THE INVENTION

The objective of the present invention is to overcome the difficulty of the high melting point of nematic triphenylene discotic liquid crystal, for example, reducing the melting point of the material and even reducing it to be below room temperature, while maintaining a wide enough range of liquid crystal temperature, by introducing three alkoxy side chains.

The present invention provides a discotic molecular compound of general formula (I) or general formula (II), and a nematic discotic liquid crystal medium comprising said discotic molecular compounds.

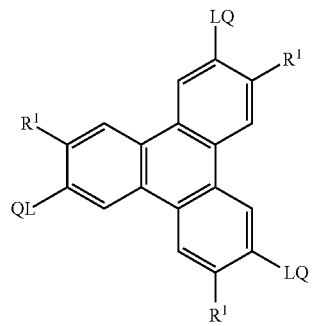

(I)

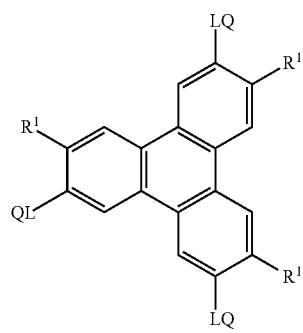

(II)

in which each group has the following meaning:

$R^1$ is selected from H, F, Cl, Br, —CN, —SCN, $OR^2$ or $SR^2$, in which $R^2$ is a straight chain or branched chain $C_{1-20}$ alkyl that may be substituted by one or more F, Cl or Br, in which one or more nonadjacent $CH_2$ groups of the straight chain or branched chain $C_{1-20}$ alkyl may be replaced by —O—, —CO—O—, —O—CO— or —O—CO—O—, provided that oxygen atoms do not directly bond to each other;

L is a linking group of the following formula:

-A1-A2-A3-A4-(A5-A4)$_a$-(A5)$_b$-(A6)$_c$-, in which A1 bonds to the triphenylene core, A1 is —O—CO—, A2 is phenylene, A3 is —O—, —O—CO—, —CO—O—, —NH—CO— or —O—CO—O—, A4 is a $C_{1-12}$ alkylene, A5 is —O—, A6 is —CO—, a=0, 1 or 2, b=0 or 1, c=0 or 1;

Q is H or a polymerizable functional group selected from a group consisting of

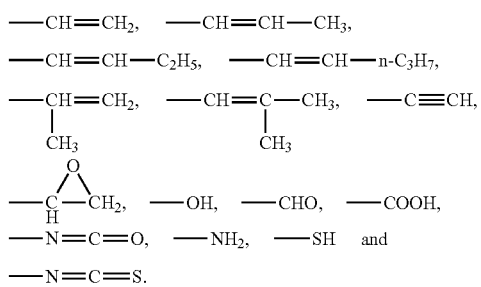

L is selected from a group consisting of the following general formulas, in which the left end of the general formula bonds to the triphenylene core.

—O—CO-Ph-O—R— (L1);
—O—CO-Ph-O—R—O— (L2);
—O—CO-Ph-O—R—CO— (L3);
—O—CO-Ph-O—R—O—CO— (L4);
—O—CO-Ph-O—R—O—R—O—CO— (L5);
—O—CO-Ph-O—R—O—R—O—R—O—CO— (L6);
—O—CO-Ph-O—CO—R- (L7);
—O—CO-Ph-O—CO—R—O— (L8);
—O—CO-Ph-O—CO—R—O—CO- (L9);
—O—CO-Ph-O—CO—R—O—Al—O—CO— (L10);
—O—CO-Ph-NH—CO—R— (L11);
—O—CO-Ph-NH—CO—R—O— (L12);
—O—CO-Ph-NH—CO—R—O—CO— (L13);
—O—CO-Ph-NH—CO—R—O—R—O—CO— (L14);
—O—CO-Ph-CO—O—R- (L15);
—O—CO-Ph-CO—O—R—O— (L16);
—O—CO-Ph-CO—O—R—O—CO— (L17);
—O—CO-Ph-CO—O—R—O—R—O—CO— (L18);
—O—CO-Ph-O—CO—O—R— (L19);
—O—CO-Ph-O—CO—O—R—O— (L20);
—O—CO-Ph-O—CO—O—R—O—CO- (L21); and
—O—CO-Ph-O—CO—O—R—O—R—O—CO- (L22);

in which, R is a $C_{1-12}$ alkylene; and Ph is a phenylene.

In another aspect of the present invention, it also provides a liquid crystal medium comprising one or more of the discotic molecular compounds of the present invention.

In another aspect of the present invention, it also provides an optical compensation film for a liquid crystal display comprising the above liquid crystal medium, and an optical compensation cell for liquid crystal display comprising the above liquid crystal medium.

Synthetic Route I:

First of all, o-dialkoxybenzene is prepared by refluxing guaiacol, bromoalkane and potassium carbonate in ethyl alcohol (or acetone) for 24~48 hours. The o-dialkoxybenzene is oxidized by ferric chloride in dichloromethane solution for 1~2 hours to obtain the mixture of hexaalkoxy-triphenylenes 1 and 2, which is separated and purified to obtain the pure substances of 1 and 2. Thiophenol and potassium carbonate are added into the compound 1 for reflux in N,N'-dimethylformamide for 1~2 hours to obtain trialkoxy trihydroxyl triphenylene 3, which further reacts with benzoic acid derivative at room temperature together with N,N'-dicyclohexylcarbodiimide (DCC) and 4-N,N-dimethylaminopyridine (DMAP) for 6~8 hours, to obtain the objective product 4.

With respect to the reactions for obtaining compound 2, see those for obtaining compound 1.

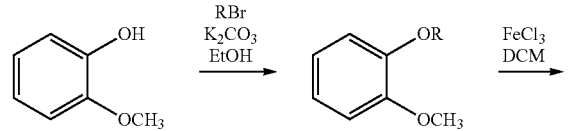

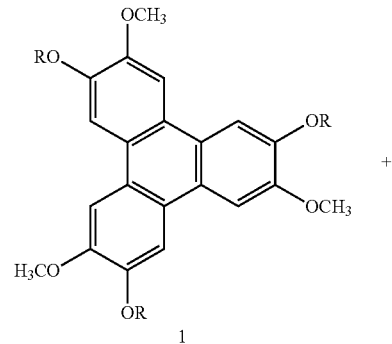

1

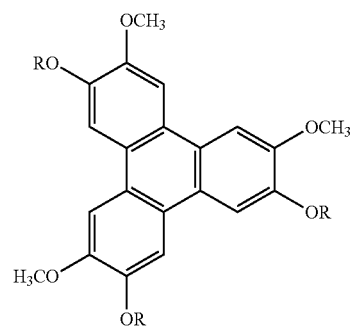

2

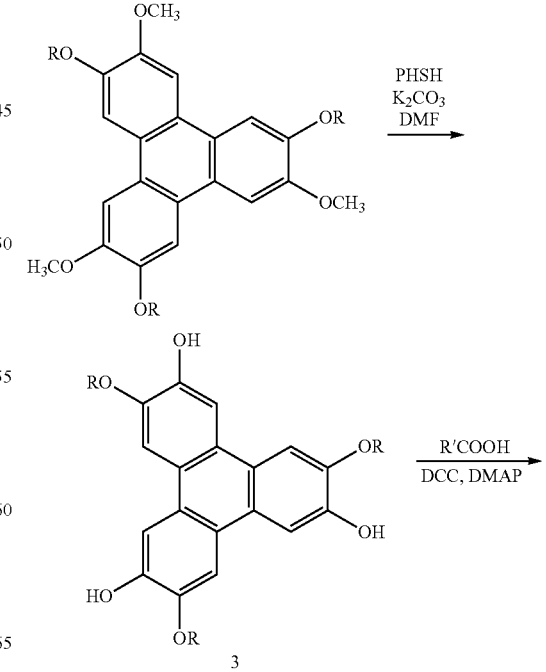

3

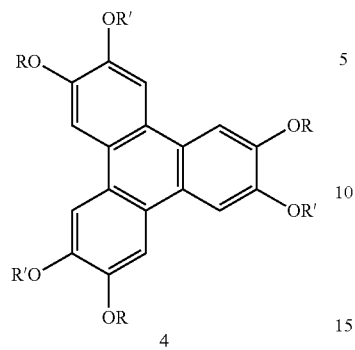

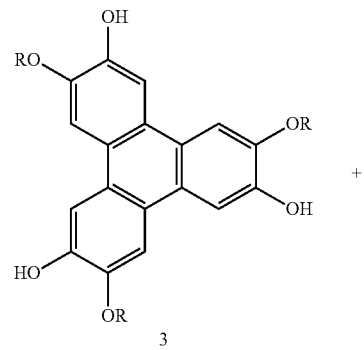

Synthetic Route II:

First of all, o-dialkoxybenzene is prepared by refluxing catechol, bromoalkane and potassium carbonate in ethyl alcohol for 24~48 h; the o-dialkoxybenzene is oxidized by ferric chloride in dichloromethane solution for about 1~2 h to obtain hexaalkoxy-triphenylene 5, which further reacts with B-bromo-9-borabicyclo[3.3.1]nonane at room temperature for 30~48 h to obtain trialkoxy trihydroxyl triphenylenes 3 and 6, and 3 is further refluxed with 5-chloro-1-phenyl-1H-tetrazole and potassium carbonate in acetone for 1218 h; moreover, a reduction reaction is performed for 24~48 h by introducing hydrogen at 40° C. and using palladium on carbon (0.35 g) as the catalyst, generating trialkoxytriphenylene 7; the product further reacts with boron tribromide at room temperature for 4~8 h to remove three alkyls, generating trihydroxytriphenylene 8; the objective product is achieved through esterification (the method is same as that of Synthetic route I) at last. With respect to the reactions for obtaining compound 6, see those for obtaining compound 3.

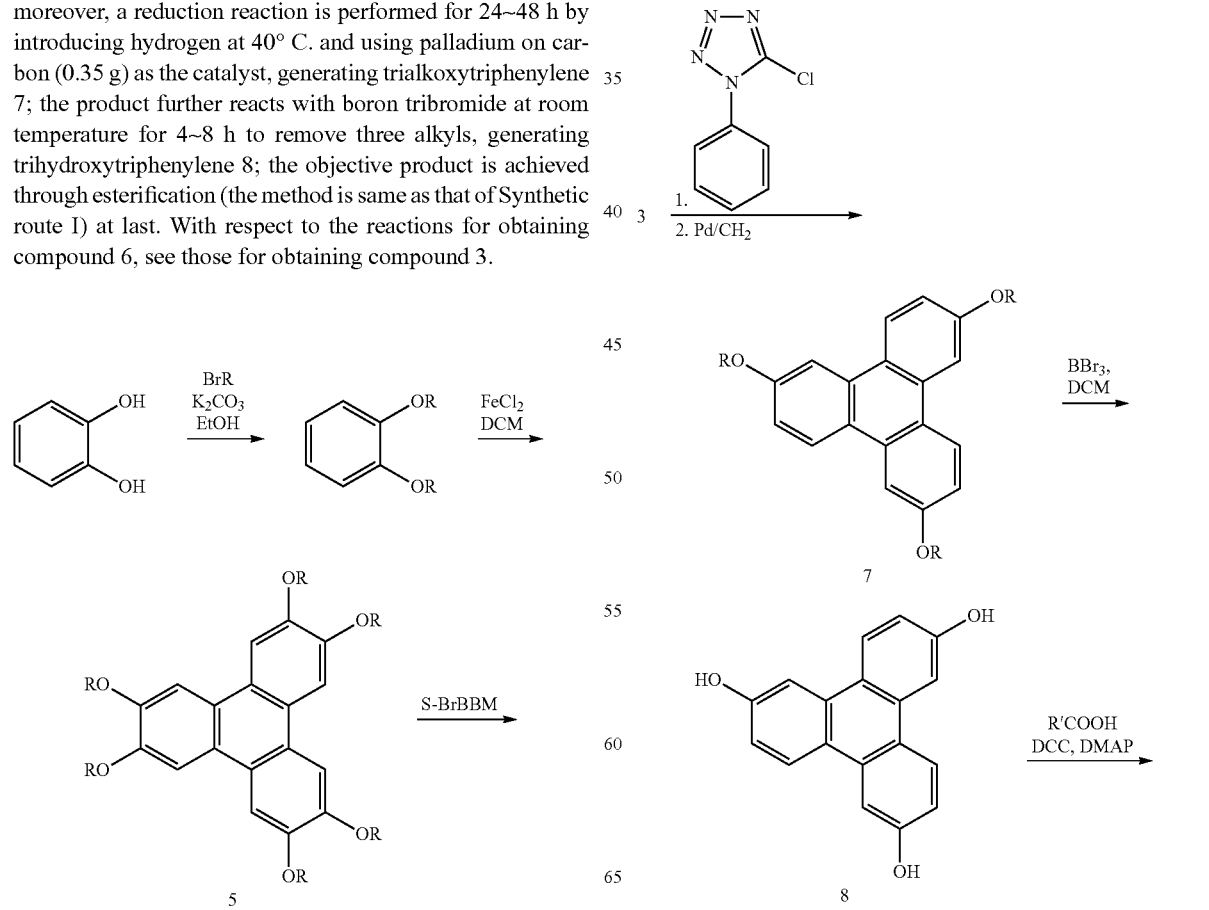

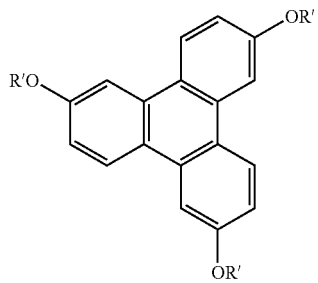

The advantage of the present invention is to synthesize the triphenylene having three ester group side chains and three alkoxy (or hydrogen) side chains by using simplified routes. The three alkoxy side chains contribute to adjusting the temperature range of the liquid crystal phase.

DETAILED EMBODIMENTS

Figure 1:
FIG. 1 is a picture of the texture of the compound of formula 7 taken during the temperature lowering process.

The present invention will be illustrated by combining the detailed embodiments below. It should be noted that, the following examples are only used to illustrate the present invention, not to limit it. Other combinations and various modifications within the conception of the present invention are possible without departing from the subject matter and scope of the present invention.

In the following examples, all the percentages are weight percentages. The temperature below is in Celsius degree. Mp represents melting point, Cp represents clearing point, h represents hour, min represents minute, Kr represents crystal phase, Ne represents nematic phase, and Is represents isotropic phase. Numbers between these symbols represent the temperature at which the transformation occurs among said phases. Alkyl is n-alkyl, unless otherwise specified. The apparatus used for $^1$H NMR is Varian 300 MHz or Bruker 300 MHz, the internal standard for test is trimethylsilane (TMS), and the solvent is deuterated chloroform ($CDCl_3$), unless otherwise specified.

Physical, physicochemical and electro-optic parameters are determined through generally known methods, such as described in "Merck Liquid Crystals—Physical Properties of Liquid Crystals—Description of the Measurement Methods".

Example 1

The compound of formula 7 is synthesized.

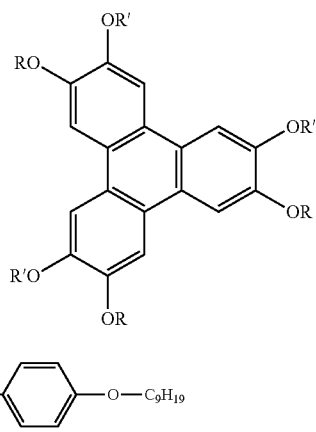

(7)

$R = \text{—} C_6H_{13}$ $R' = \text{—} CO\text{—}\phantom{x}\text{—}O\text{—}C_9H_{19}$ Reaction Step 1.1

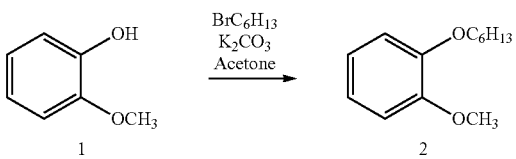

The compound of formula 1 (6.4 g, 0.05 mol), 1-bromohexane (12.4 g, 0.075 mol) and potassium carbonate (13.8 g, 0.1 mol) are refluxed in dry acetone (60 ml) for 48 h. The temperature is lowered to room temperature, and the suction filtration is performed. The filter cake is washed with acetone; the filter liquor, from which the solvent is removed, is distillated under reduced pressure, and the fractions of 105-110° C. (the vacuum degree is about 8 mm mercury column) are collected. The obtained compound of formula 2 is colourless oily matter (9.9 g), and the yield is 95%.

$^1$H NMR, δ: 6.90 (s, 4H), 4.01 (t, 2H, J=6.6 Hz), 3.87 (s, 3H), 1.85 (m, 2H), 1.47-1.32 (m, 6H), 0.91 (t, 3H, J=6.9 Hz).

Reaction Step 1.2

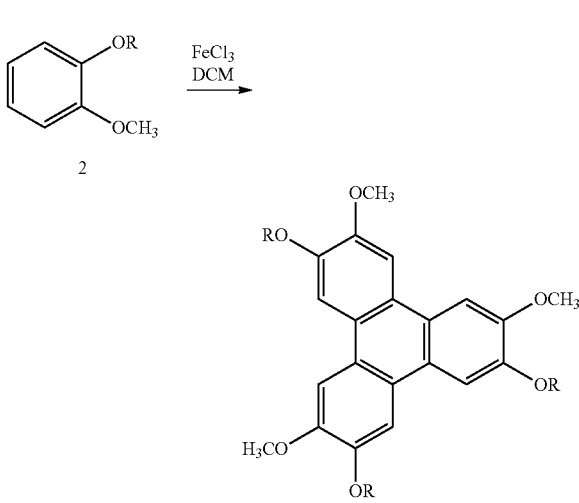

$R = C_6H_{13}$

The compound of formula 2 (1.04 g, 5 mmol) and ferric chloride (1.95 g, 12 mmol) are stirred in dichloromethane (DCM) (22 ml) for 1.5 h at room temperature, which then is transferred into methyl alcohol (90 ml). The generated precipitate is filtrated, and the crude product is purified with silica gel column (dichloromethane/petroleum ether in a volume ratio of 1:1~3:2). The obtained compound of formula 3 is colourless solid (0.46 g), and the yield is 45%.

$^1$H NMR, δ: 7.85 (s, 1H), 7.83 (s, 4H), 7.82 (s, 1H), 4.26 (t, 6H, J=6.9 Hz), 4.11 (s, 9H), 2.03-1.93 (m, 6H), 1.62-1.54 (m, 6H), 1.43-1.37 (m, 12H), 0.94 (t, 9H, J=6.9 Hz).

Reaction Step 1.3

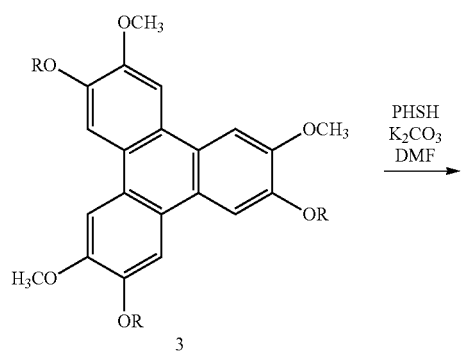

R = $C_6H_{13}$

The compound of formula 3 (0.83 g, 1.34 mmol), thiophenol (0.88 g, 8 mmol) and potassium carbonate (1.66 g, 12 mmol) are refluxed in N,N-dimethylformamide (DMF) (6 ml) for 1.5 h under the protection of $N_2$. The mixture is cooled to room temperature and acidized by diluted hydrochloric acid (30 ml). The generated precipitate is filtrated, and the crude product is purified with silica gel column (the eluent is dichloromethane/petroleum ether in a volume ratio of 2:1). The obtained compound of formula 4 is colourless solid (0.34 g), and the yield is 44%.

$^1$H NMR, δ: 7.91 (s, 1H), 7.90 (s, 1H), 7.88 (s, 1H), 7.72 (s, 1H), 7.60 (s, 1H), 7.59 (s, 1H), 5.88 (s, 1H), 5.87 (s, 1H), 5.85 (s, 1H), 4.22-4.14 (m, 6H), 1.96-1.82 (m, 6H), 1.61-1.39 (m, 18H), 0.94 (t, 9H, J=6.6 Hz).

Reaction Step 1.4

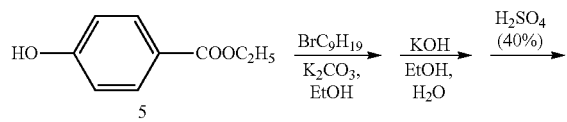

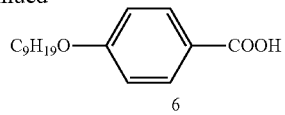

The compound of formula 5 (15 g, 90.27 mmol), 1-bromononane (24.3 g, 117.4 mmol) and potassium carbonate (18.7 g, 135.5 mmol) are refluxed in dry absolute ethyl alcohol (90 ml) for 48 h. The temperature is lowered to room temperature, and the suction filtration is performed. The filter cake is washed with ethyl alcohol; part of the solvent is removed from the filter liquor, water (36 ml) and sodium hydroxide (30.7 g) are added into the filter liquor, and the mixture is refluxed for 1.5 h. The mixture is then cooled to room temperature and acidized by 40% sulfuric acid. The generated precipitate is filtrated, and the crude product is recrystallized with ethyl alcohol. The obtained compound of formula 6 is colourless powder (20 g), and the yield is 84%.

$^1$H NMR, δ: 8.09 (d, 2H, J=8.7 Hz), 6.97 (d, 2H, J=8.7 Hz), 4.07 (t, 2H, J=6.3 Hz), 1.85 (m, 2H), 1.49-1.30 (m, 12H), 0.91 (t, 3H, J=6.9 Hz).

Reaction Step 1.5

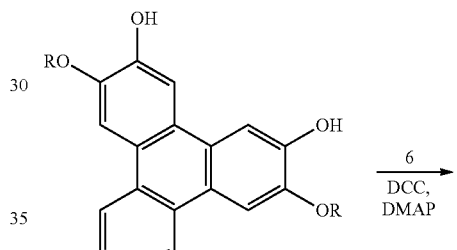

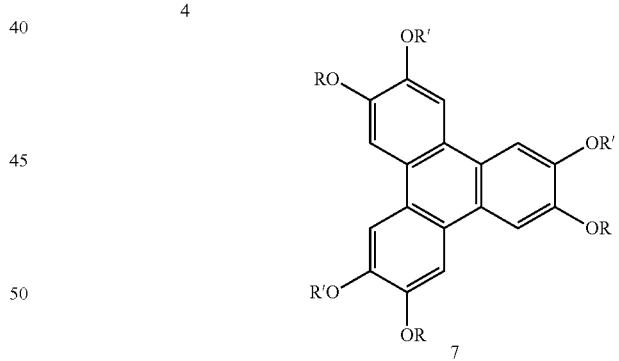

R = —$C_8H_{18}$

R' = —CO—⌬—O—$C_8H_{18}$

The compound of formula 4 (0.2 g, 0.347 mmol), the compound of formula 6 (0.734 g, 2.78 mmol) and N,N'-dicyclohexyl-carbodiimide (DCC) (0.57 g, 2.88 mmol) are added into tetrahydrofuran (5 ml), and dimethylaminopyridine (DMAP) (catalytic amount) is also added. The mixture reacts overnight at room temperature. After filtration, the filter cake is washed with dichloromethane (20 ml); the filter liquor is dried by rotary evaporation. The crude product is purified with silica gel column (the eluent is petroleum ether/ ethyl acetate in a volume ratio of 4:1). The obtained compound of formula 7 is colourless solid (0.36 g), and the yield is 80%.

$^1$H NMR, δ: 8.21 (s, 1H), 8.19-8.13 (m, 6H), 7.98 (s, 1H), 7.94 (s, 1H), 7.89 (s, 1H), 7.85 (s, 1H), 7.75 (s, 1H), 6.96-6.90 (m, 6H), 4.22-4.12 (m, 6H), 4.06-4.02 (m, 6H), 1.85-1.80 (m, 6H), 1.72-1.67 (m, 6H), 1.54-1.19 (m, 60H), 0.99-0.78 (m, 18H).

The compound is tested with a polarizing microscope. The melting point of the compound is 90° C. and the clearing point thereof is 107° C. The compound forms a discotic liquid crystal nematic phase when lowering the temperature. See FIG. 1 for the texture thereof.

Example 2

The compound of formula 12 is synthesized.

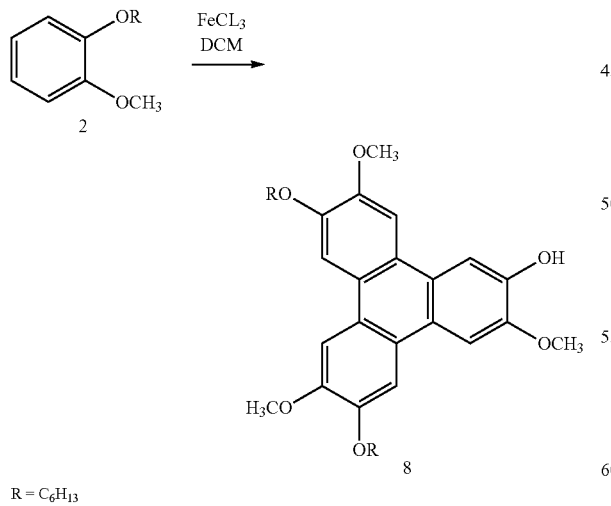

R = —C$_6$H$_{13}$
R' = —CO—⟨benzene⟩—O—C$_6$H$_{12}$—O—CO—CH=CH$_2$

Reaction Step 2.1 Reaction step 2.1 is same as Reaction step 1.1.

Reaction Step 2.2

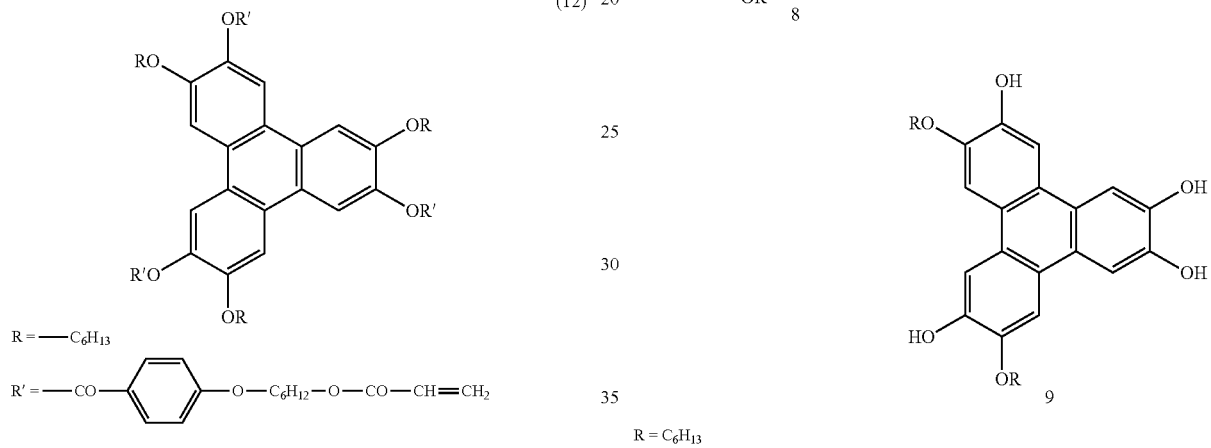

R = C$_6$H$_{13}$

The detailed steps of reaction step 2.2 are similar to those of reaction step 1.2, through which the compound of formula 8 is obtained. The compound of formula 8 is colourless solid, and the reaction yield thereof is 5%.

$^1$H NMR, δ: 7.74 (s, 3H), 7.71 (s, 3H), 4.21 (t, 6H, J=6.8 Hz), 4.07 (s, 9H), 1.98-1.91 (m, 6H), 1.56-1.51 (m, 6H), 1.38-1.37 (m, 12H), 0.91 (t, 9H, J=6.8 Hz).

Reaction Step 2.3

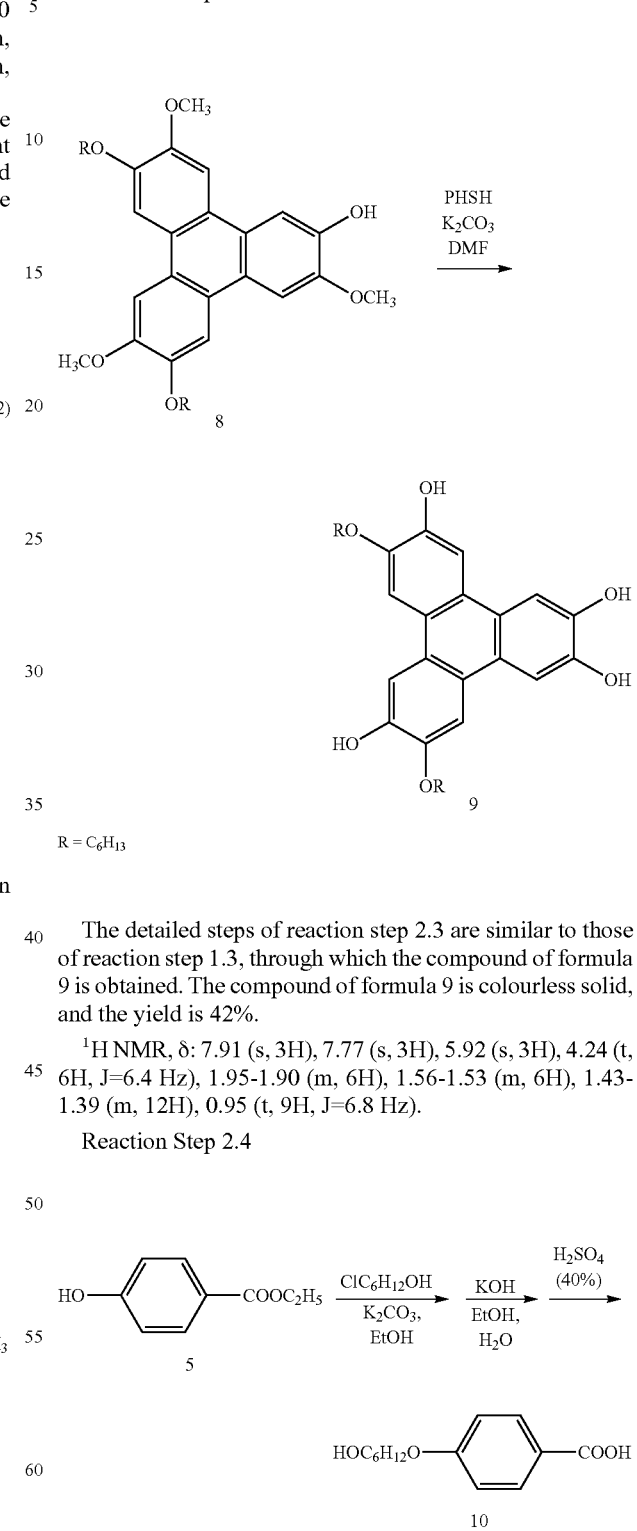

R = C$_6$H$_{13}$

The detailed steps of reaction step 2.3 are similar to those of reaction step 1.3, through which the compound of formula 9 is obtained. The compound of formula 9 is colourless solid, and the yield is 42%.

$^1$H NMR, δ: 7.91 (s, 3H), 7.77 (s, 3H), 5.92 (s, 3H), 4.24 (t, 6H, J=6.4 Hz), 1.95-1.90 (m, 6H), 1.56-1.53 (m, 6H), 1.43-1.39 (m, 12H), 0.95 (t, 9H, J=6.8 Hz).

Reaction Step 2.4

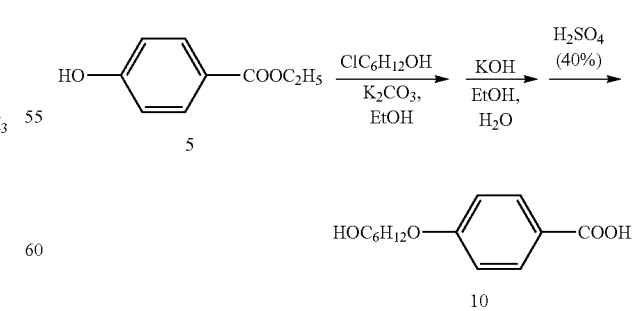

The detailed steps of reaction step 2.4 are similar to those of reaction step 1.4. The obtained compound of formula 10 is colourless powder, and the yield is 83%.

Reaction Step 2.5

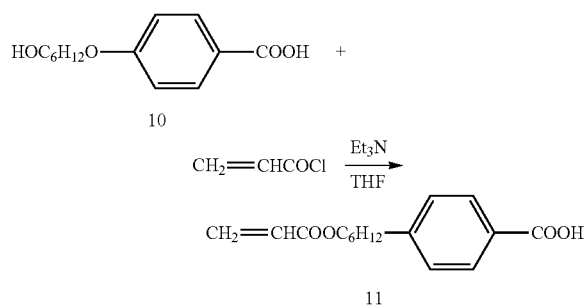

The compound of formula 10 (10 g, 42 mmol) is added into triethylamine (5 ml) and tetrahydrofuran (30 ml), and acryloyl chloride (6.6 g, 63 mmol) is dropwise added in 0.5 h. The mixture reacts overnight at room temperature, and then is transferred into water (150 ml). The generated precipitate is filtrated, and the crude product is recrystallized with ethyl alcohol. The obtained compound of formula 11 is colourless powder (8.2 g), and the yield is 64%.

$^1$H NMR, δ: 8.06 (d, 2H, J=8.7 Hz), 6.93 (d, 2H, J=8.7 Hz), 6.48 (dd, 1H, J=1.5, 17.4 Hz), 6.21 (dd, 1H, J=10.2, 17.4 Hz), 5.86 (dd, 1H, J=1.5, 10.2 Hz), 4.17 (t, 2H, J=6.6 Hz), 4.05 (t, 2H, J=6.6 Hz), 1.85-1.81 (m, 2H), 1.75-1.70 (m, 2H), 1.53-1.46 (m, 4H).

Reaction Step 2.6

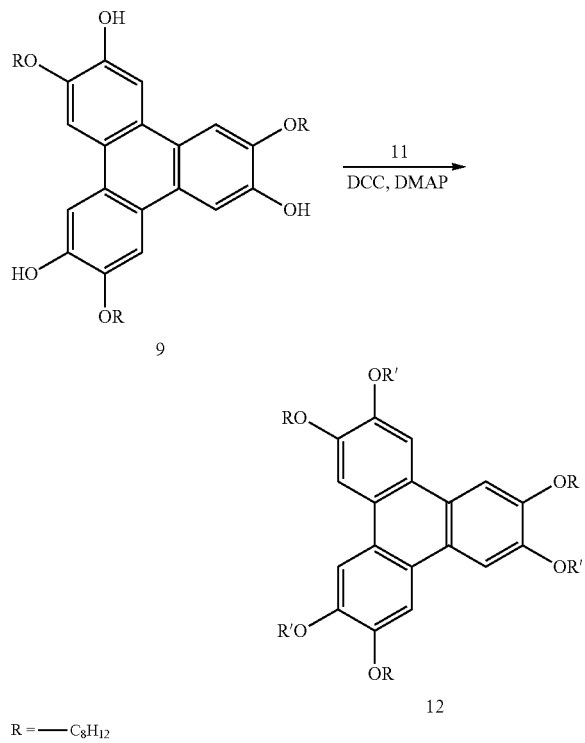

The compound of formula 9 (0.12 g, 0.208 mmol), the compound of formula 11 (0.49 g, 1.67 mmol) and DDC (0.34 g, 1.67 mmol) are added into dichloromethane (5 ml), and DMAP (catalytic amount) is also added. The mixture reacts overnight at room temperature. After filtration, the filter cake is washed with dichloromethane; the filter liquor is dried by rotary evaporation. The crude product is purified with silica gel column (the eluent is dichloromethane/ethyl acetate in a volume ratio of 100:1). The obtained compound of formula 12 is colourless solid (0.24 g), and the yield is 84%.

$^1$H NMR, δ: 8.15 (s, 3H), 8.11 (d, 6H, J=7.2 Hz), 7.72 (s, 3H), 6.88 (d, 6H, J=7.2 Hz), 6.45 (dd, 3H, J=1.5, 17.4 Hz), 6.19 (dd, 3H, J=10.2, 17.4 Hz), 5.85 (dd, 3H, J=1.5, 10.2 Hz), 4.22 (m, 12H), 4.03 (t, 6H, J=6.3 Hz), 1.88-1.68 (m, 18H), 1.60-1.53 (m, 12H), 1.49-1.12 (m, 18H), 0.78 (t, 9H, J=6.8 Hz).

Figure 2:
FIG. 2 is a picture of the texture of the compound of formula 12 taken during the temperature rising process.

The compound is tested with a polarizing microscope. The melting point of the compound is 92° C. and the clearing point thereof is 134° C. The compound forms a discotic liquid crystal nematic phase when elevating the temperature. See FIG. 2 for the texture thereof.

Example 3

The compound of formula 19 is synthesized.

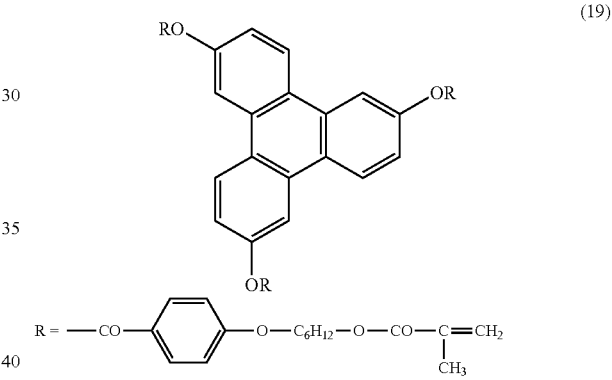

Reaction Step 3.1

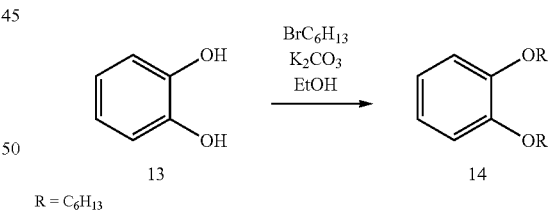

The compound of formula 13 (20 g, 0.1816 mol), 1-bromo-n-hexane (89.9 g, 0.5448 mol), anhydrous potassium carbonate (75.3 g, 0.5448 mol) and potassium iodide (6.0 g) are refluxed in absolute ethyl alcohol (250 ml) for 48 h. The temperature is lowered to room temperature, and the suction filtration is performed. The filter cake is washed with acetone (150 ml) twice; the filter liquor is first concentrated and then distillated under reduced pressure, and the fractions of 149-157° C. (0.7 mmHg) are collected. The obtained compound of formula 14 is colourless oily liquid (48 g), and the yield is 96%.

$^1$H NMR, δ: 6.89 (s, 4H), 3.99 (t, 4H, J=6.9 Hz), 1.83-1.76 (m, 4H, J=6.9 Hz), 1.49-1.31 (m, 12H), 0.9 (t, 6H, J=6.9 Hz).

Reaction Step 3.2

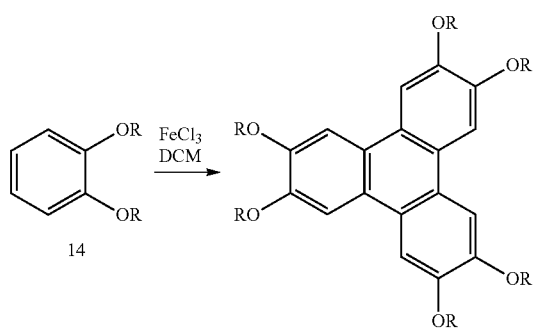

R = C$_8$H$_{13}$

The compound of formula 14 (21.3 g, 76.6 mmol) and ferric chloride (41.0 g, 252.84 mmol) are stirred in DCM (510 ml) for 1.5 h at room temperature, which then are transferred into the mixture of methyl alcohol (100 ml) and ice (200 g). The crude product is purified with silica gel column (ethyl acetate/petroleum ether in a volume ratio of 1:50). The obtained compound of formula 15 is colourless solid (13.3 g), and the yield is 63%.

$^1$H NMR, δ: 7.84 (s, 6H), 4.23 (t, 12H, J=6.9 Hz), 1.94 (t, 12H, J=6.9 Hz), 1.58-1.38 (m, 36H), 0.94 (t, 18H, J=6.9 Hz).

Reaction Step 3.3

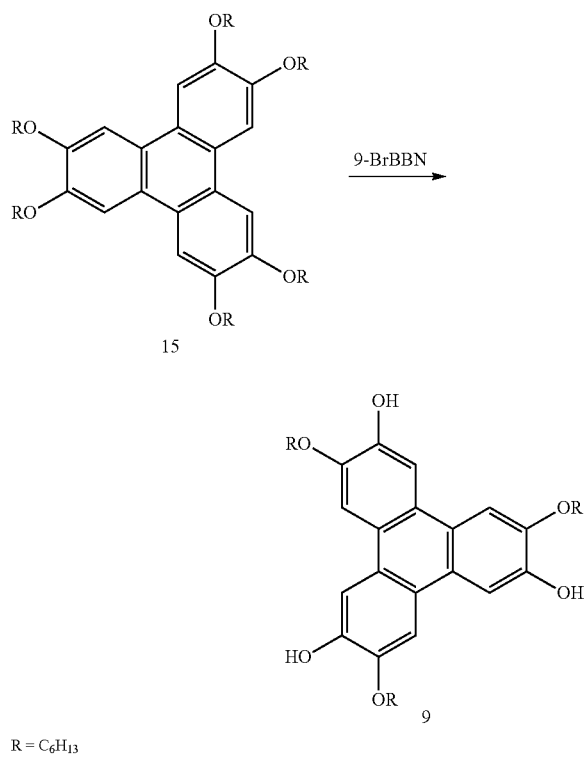

R = C$_6$H$_{13}$

The compound of formula 15 (3 g, 3.4 mmol) and B-bromo-9-borabicyclo-[3.3.1]nonane (16.3 mmol, which is in 16.3 ml dichloromethane solution with a concentration of 1 mol dm$^{-3}$) react at room temperature for 30 h under the protection of argon gas. Thereafter, 2-aminoethanol (1 ml) is slowly added, and then water (20 ml) is added. The mixture is extracted three times with dichloromethane (50 ml). The organic layer is dried with anhydrous MgSO$_4$ and then the solvent is removed therefrom. The crude product is purified with silica gel column (dichloromethane/petroleum ether in a volume ratio of 3:2). The obtained compound of formula 9 is colourless powder (0.94 g), and the yield is 38%.

Reaction Step 3.4

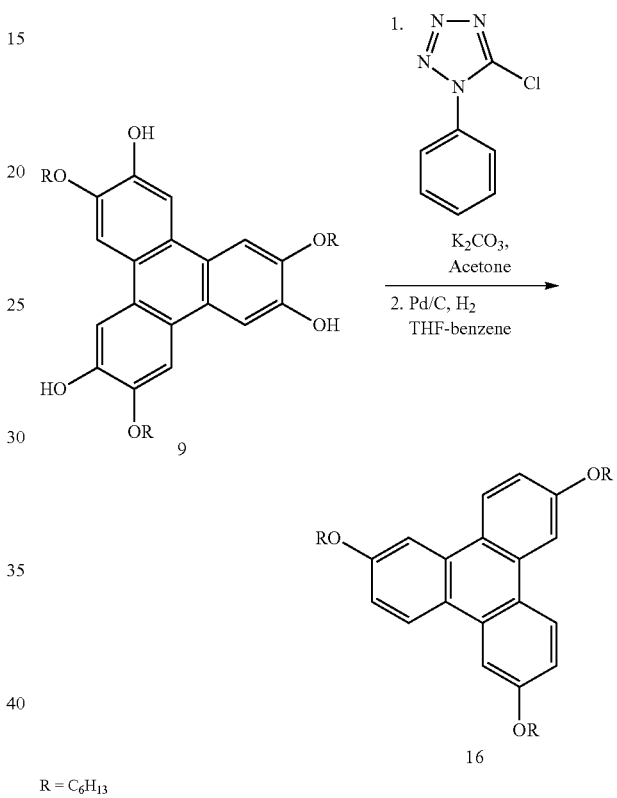

R = C$_6$H$_{13}$

The compound of formula 9 (5.8 g, 10 mmol), 5-chloro-1-phenyl-1H-tetrazole (1.81 g, 10 mmol) and potassium carbonate (2.76, 20 mmol) are refluxed in acetone (40 ml) for 18 h under the protection of nitrogen gas. The mixture is cooled to room temperature, and the filtration is performed. The filter cake is washed with acetone (30 ml); the filter liquor is transferred into 140 ml water. The generated precipitate is filtrated and dried under reduced pressure, and 7 g of crude product is obtained. The crude product is dissolved in tetrahydrofuran (20 ml) and benzene (20 ml), palladium on carbon (0.35 g) is added, and then hydrogen is fed thereinto. The mixture reacts for 24 h at 40° C. The temperature is lowered to room temperature, and the filtration is performed. The solvent is removed by rotary evaporation, and the crude product is purified with silica gel column (dichloromethane/petroleum ether in a volume ratio of 1:3). The obtained compound of formula 16 is colourless powder (4.3 g), and the yield is 81%.

$^1$H NMR, δ: 8.43 (d, 3H, J=9.0 Hz), 7.92 (d, 3H, J=2.4 Hz), 7.19 (dd, 3H, J=9.0, 2.4 Hz), 4.16 (t, 6H, J=6.6 Hz), 1.93 (m, 6H), 1.55-1.51 (m, 6H), 1.39-1.37 (m, 12H), 0.93 (t, 9H, J=6.6 Hz).

Reaction Step 3.5

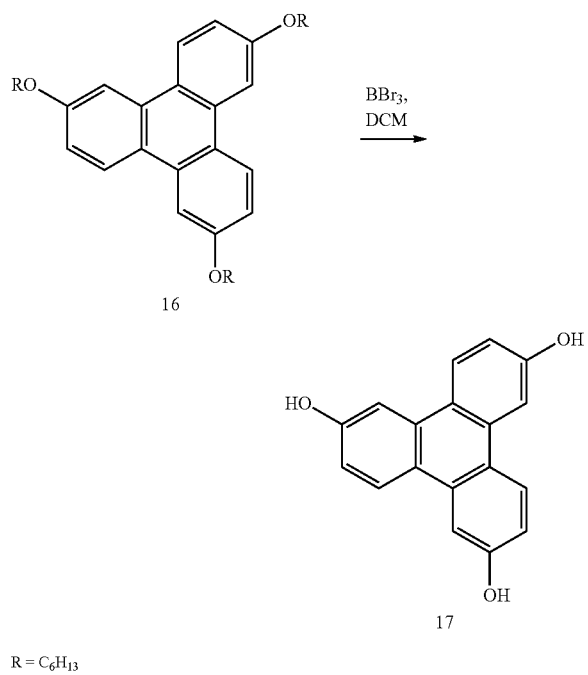

R = C₆H₁₃

The compound of formula 16 (0.53 g, 1 mmol) is added into dry dichloromethane (15 ml) under the protection of nitrogen, the temperature is lowered to 0° C., and then boron tribromide (1.5 g, 6 mmol) is dropwise added. The temperature is naturally elevated to room temperature, and then the mixture is transferred into ice water. The generated precipitate is filtrated, and then is dried under reduced pressure. The obtained compound of formula 17 is light grey powder (0.28 g), and the yield is 100%.

$^1$H NMR (CD$_3$OD) δ: 8.36 (d, 3H, J=9.0 Hz), 7.86 (d, 3H, J=2.4 Hz), 7.07 (dd, 3H, J=9.0, 2.4 Hz).

Reaction Step 3.6

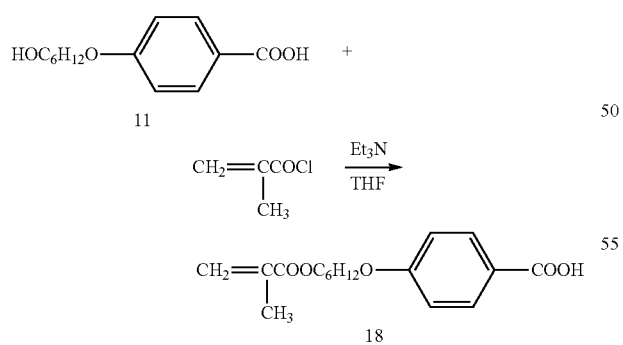

The detailed steps of reaction step 3.6 are similar to those of reaction step 2.5. The obtained compound of formula 8 is colourless powder, and the yield is 90%.

$^1$H NMR, δ: 8.06 (d, 2H, J=9.0 Hz), 6.94 (d, 2H, J=9.0 Hz), 6.09 (s, 1H), 5.55 (s, 1H), 4.19 (t, 2H, J=6.6 Hz), 4.05 (t, 2H, J=6.6 Hz), 1.94 (s, 3H), 1.85-1.70 (m, 4H), 1.53-1.46 (m, 4H).

Reaction Step 3.7

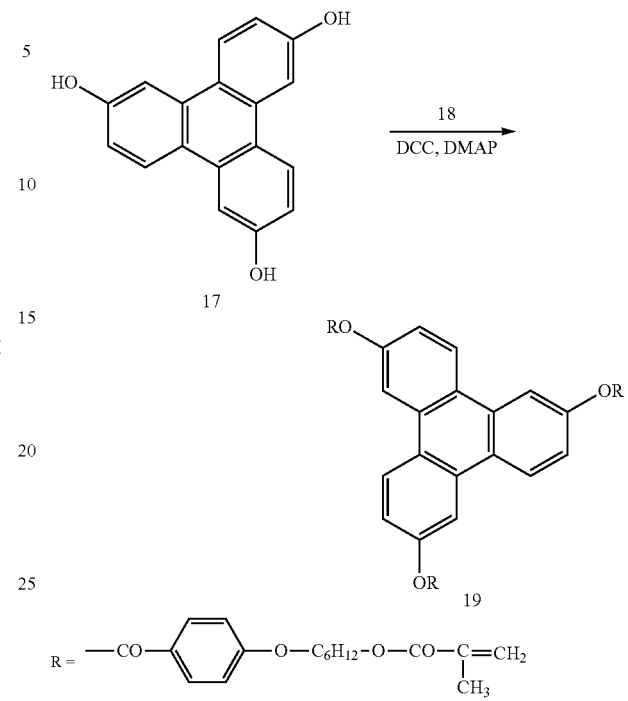

Under the protection of nitrogen, the compound of formula 17 (0.1 g, 0.36 mmol) is added into dry tetrahydrofuran (10 ml), and the compound of formula 18 (0.5 g, 1.62 mmol), DDC (0.33 g, 1.62 mmol) and DMAP (catalytic amount) are also added. The mixture reacts overnight at room temperature. After filtration, the filter liquor is dried by rotary evaporation to obtain the crude product. The crude product is purified with silica gel column (dichloromethane/ethyl acetate in a volume ratio of 60:1). The obtained compound of formula 19 is colourless powder (0.26 g), and the yield is 65%.

$^1$H NMR, δ: 8.60 (d, 3H, J=9.0 Hz), 8.42 (s, 3H), 8.24 (d, 6H, J=9.0 Hz), 7.54 (d, 3H, J=9.0 Hz), 7.16 (d, 6H, J=9.0, 2.4 Hz), 6.11 (s, 3H), 5.56 (s, 3H), 4.20 (t, 6H, J=6.6 Hz), 4.10 (t, 6H, J=6.6 Hz), 2.17 (s, 9H), 1.95-1.70 (m, 12H), 1.61-1.50 (m, 12H).

The compound is tested with a polarizing microscope. The compound is waxy solid at room temperature and the melting point thereof is 134° C.

Example 4

The compound of formula 23 is synthesized.

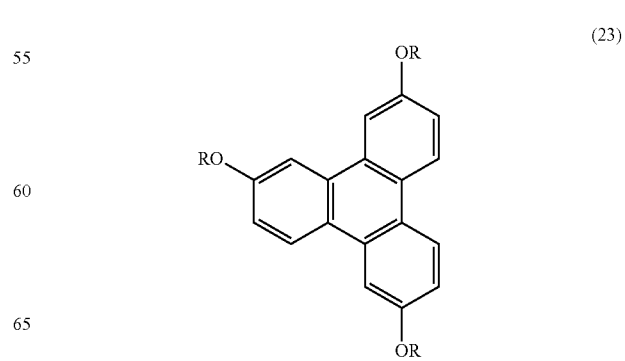

(23)

-continued

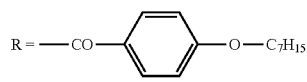

Reaction Step 4.1

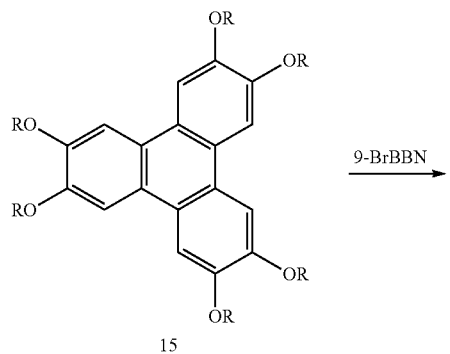

The detailed steps of reaction step 4.1 are similar to those of reaction step 3.3. The obtained compound of formula 4 is colourless powder, and the yield is 45%.

Reaction Step 4.2

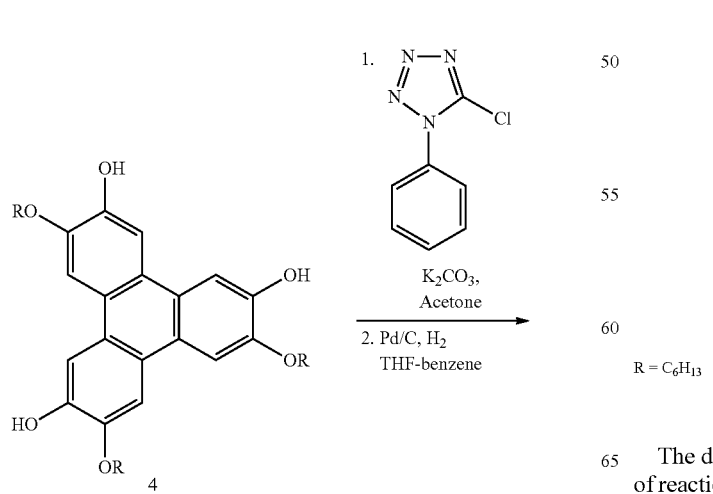

-continued

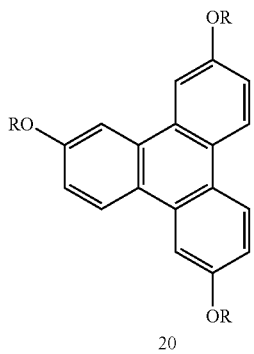

The detailed steps of reaction step 4.2 are similar to those of reaction step 3.4. The obtained compound of formula 20 is colourless powder, and the yield is 45%.

$^1$H NMR, δ: 8.50 (d, 2H, J=9.0 Hz), 8.44 (d, 1H, J=9.0 Hz), 7.96 (s, 1H), 7.95 (s, 2H), 7.28 (d, 2H, J=9.0 Hz), 7.22 (d, 1H, J=9.0 Hz), 4.23 (m, 6H), 1.95-1.91 (m, 6H), 1.58-1.55 (m, 6H), 1.43-1.4 (m, 12H), 0.98-0.96 (m, 9H).

Reaction Step 4.3

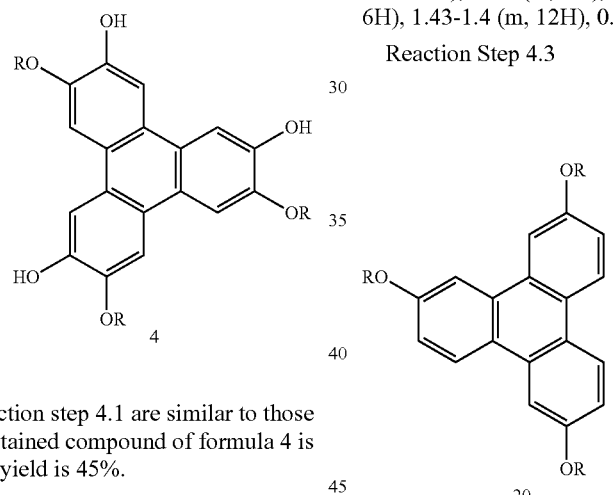

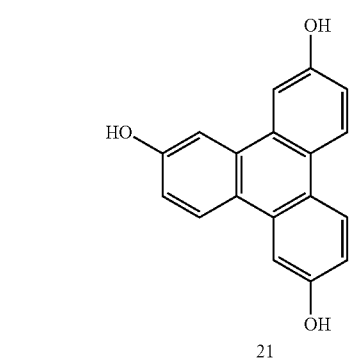

The detailed steps of reaction step 4.3 are similar to those of reaction step 3.5. The obtained compound of formula 21 is colourless powder, and the yield is 100%.

Reaction Step 4.4

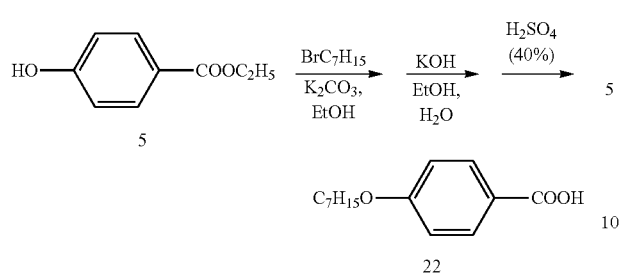

The detailed steps of reaction step 4.4 are similar to those of reaction step 1.4. The obtained compound of formula 22 is colourless powder, and the yield is 82%.

$^1$H NMR, δ: 8.07 (d, 2H, J=9.0 Hz), 6.95 (d, 2H, J=9.0 Hz), 4.04 (t, 2H, J=6.6 Hz), 1.85-1.76 (m, 2H), 1.49-1.31 (m, 8H), 0.92 (t, 3H, J=6.6 Hz).

Reaction Step 4.5

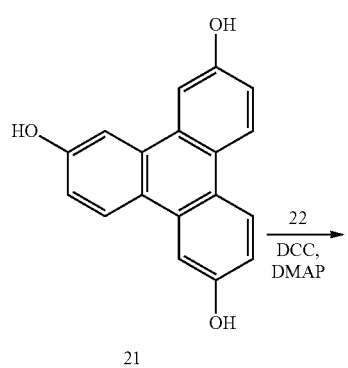

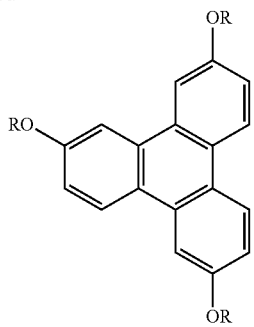

The detailed steps of reaction step 4.5 are similar to those of reaction step 1.5. The obtained compound of formula 23 is colourless powder, and the yield is 81%.

$^1$H NMR, δ: 8.1 (d, 2H, J=9.0 Hz), 8.61 (d, 1H, J=9.0 Hz), 8.41 (s, 1H), 8.36 (s, 2H), 8.25-8.19 (m, 6H), 7.55 (s, 2H), 7.53 (s, 1H), 7.03-6.98 (m, 6H), 4.10-4.04 (m, 6H), 1.85-1.82 (m, 6H), 1.49-1.25 (m, 24H), 0.91 (m, 9H).

The compound is tested with a polarizing microscope. The compound is waxy solid at room temperature and the melting point thereof is 183° C.

| No. | Structures of Compounds | Melting Point | Clearing Point | References |
|---|---|---|---|---|
| 7 | 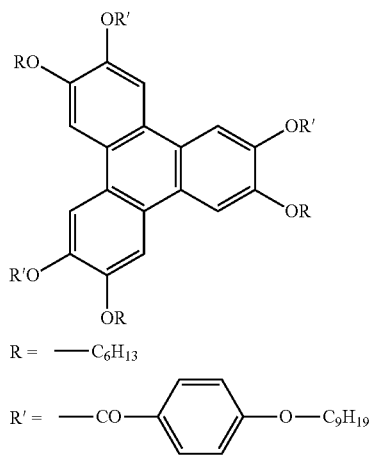 | 90 | 107 | — |

-continued
| No. | Structures of Compounds | Melting Point | Clearing Point | References |
|---|---|---|---|---|
| 12 | 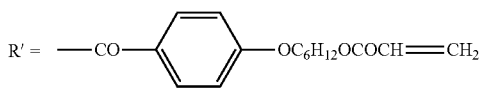 R = —C₆H₁₃<br>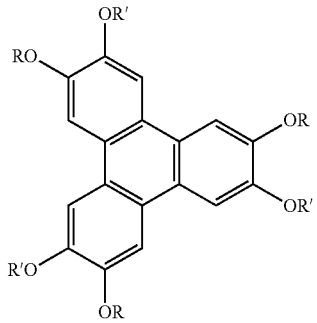R' = —CO—⟨phenyl⟩—OC₆H₁₂OCOCH═CH₂ | 92 | 134 | — |
| 19 | 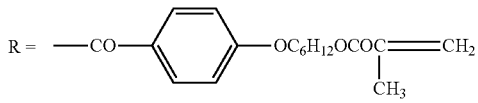<br>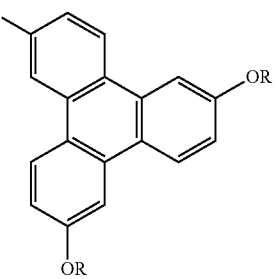R = —CO—⟨phenyl⟩—OC₆H₁₂OCOC(CH₃)═CH₂ | 134 | none | — |
| 23 | 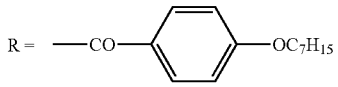<br>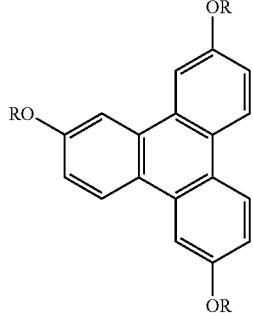R = —CO—⟨phenyl⟩—OC₇H₁₅ | 183 | none | — |

-continued
| No. | Structures of Compounds | Melting Point | Clearing Point | References |
|---|---|---|---|---|
| a | 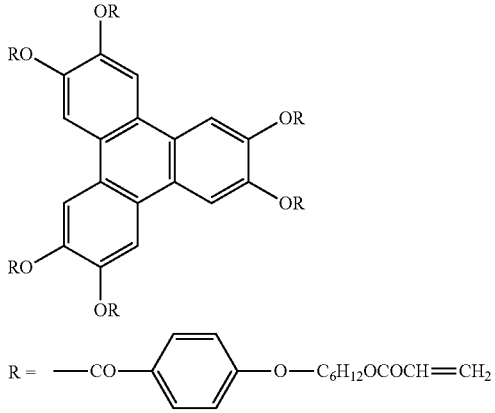 R = —CO—⌬—O—C₆H₁₂OCOCH=CH₂ | 112 | 180 | Polym. Adv. Technol. 2000, 11, 398-403 |
| b | 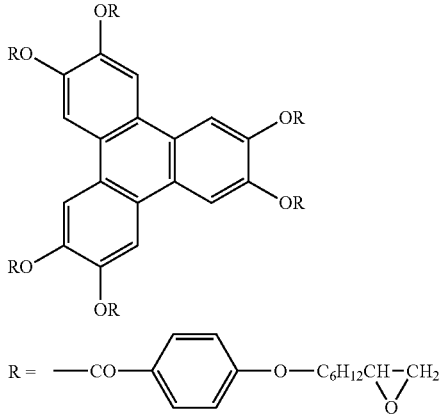 R = —CO—⌬—O—C₆H₁₂CH—CH₂ (epoxide) | 114 | 220 | Polym. Adv. Technol. 2000, 11, 398-403 |
| c | 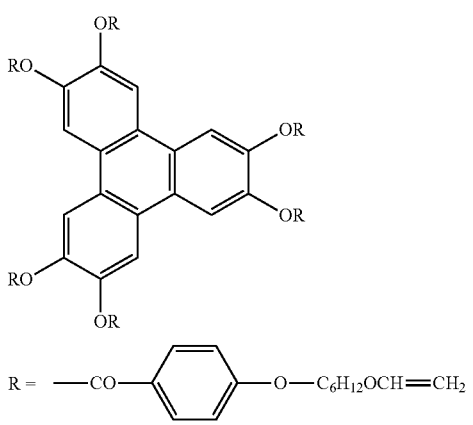 R = —CO—⌬—O—C₆H₁₂OCH=CH₂ | 132 | 217 | Polym. Adv. Technol. 2000, 11, 398-403 |

It can be seen from the above table that the clearing points of the triphenylene derivatives provided by the present invention are much lower than those of the existing materials, and thus energy saving and preparation process simplifying can be achieved.

What is claimed is:

1. A discotic molecular compound of general formula (I) or general formula (II),

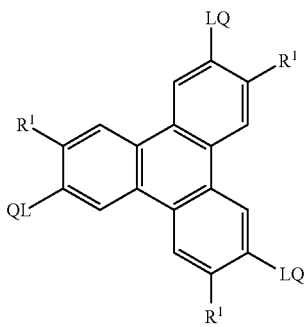
(I)

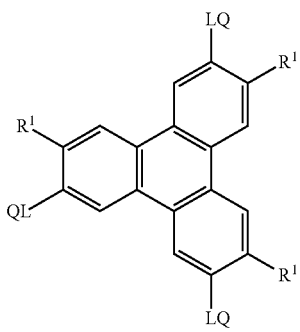
(II)

wherein:
R$^1$ is selected from the group consisting of H or OR$^2$, in which R$^2$ is a straight chain or branched chain C$_{1-20}$ alkyl;

L is a linking group of the following formula:

-A1-A2-A3-A4-(A5-A4)$_a$-(A5)$_b$-(A6)$_c$-, in which A1 bonds to the triphenylene core, A1 is —O—CO—, A2 is phenylene, A3 is —O—, A4 is a C$_{1-12}$ alkylene, A5 is —O—, and A6 is —CO—, a=0, b=0 or 1, c=0 or 1;

Q is H or a polymerizable functional group selected from the group consisting of

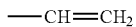

and

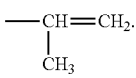

2. The discotic molecular compound of claim 1, where said L is selected from the group consisting of the following general formulas:

—O—CO-Ph-O—R— (L1);

and

—O—CO-Ph-O—R—O—CO— (L4);

wherein:
R is a C$_{1-12}$ alkylene; and
Ph is a phenylene.

3. The discotic molecular compound of claim 2 selected from the group of discotic molecular compounds consisting of the following compounds:

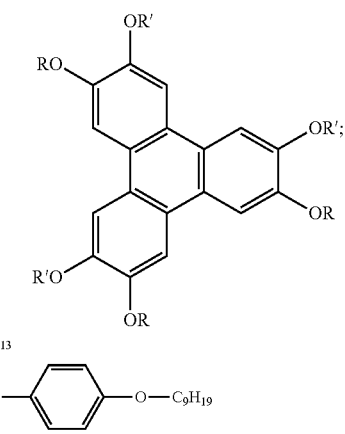
(7)

R = —C$_6$H$_{13}$

R' = —CO—⟨Ph⟩—O—C$_9$H$_{19}$

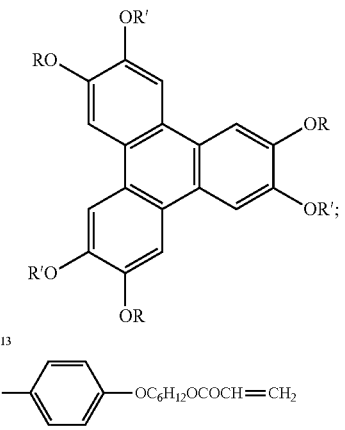
(12)

R = —C$_6$H$_{13}$

R' = —CO—⟨Ph⟩—OC$_6$H$_{12}$OCOCH═CH$_2$

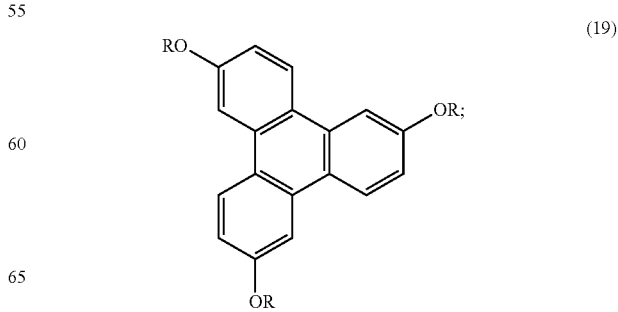
(19)

-continued
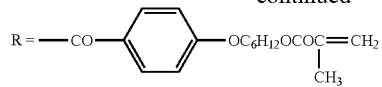
and
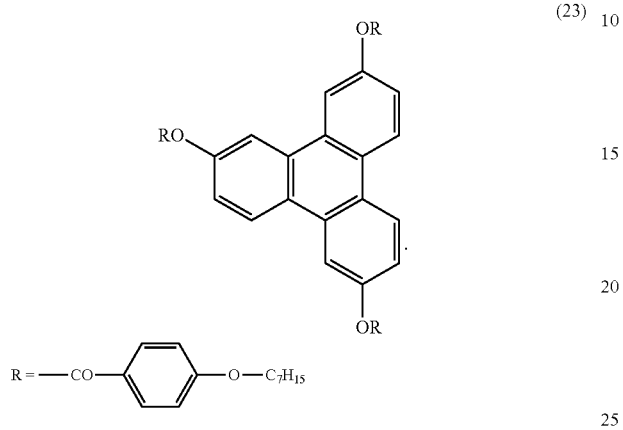
4. A liquid crystal medium, comprising one or more of the discotic molecular compounds according to claim 1.
5. An optical compensation film for a liquid crystal display, comprising the liquid crystal medium according to claim 4.
6. An optical compensation cell for a liquid crystal display, comprising the liquid crystal medium of claim 4.
* * * * *